(12) United States Patent
Suehara et al.

(10) Patent No.: US 9,827,000 B2
(45) Date of Patent: Nov. 28, 2017

(54) TREATMENT INSTRUMENT FOR MEDICAL USE

(71) Applicant: Terumo Kabushiki Kaisha, Tokyo (JP)

(72) Inventors: Satoru Suehara, Kaisei-machi (JP); Taiga Nakano, Isehara (JP); Kenichi Kumoyama, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 320 days.

(21) Appl. No.: 14/517,621

(22) Filed: Oct. 17, 2014

(65) Prior Publication Data
US 2015/0112134 A1    Apr. 23, 2015

(30) Foreign Application Priority Data

Oct. 18, 2013 (JP) .................................. 2013-217557

(51) Int. Cl.
   *A61B 1/005* (2006.01)
   *A61B 1/00* (2006.01)
   *A61B 17/24* (2006.01)
   *A61B 17/00* (2006.01)

(52) U.S. Cl.
   CPC ............ *A61B 17/24* (2013.01); *A61B 1/0052* (2013.01); *A61B 1/0055* (2013.01); *A61B 1/00082* (2013.01); *A61B 1/00135* (2013.01); *A61B 1/00154* (2013.01); *A61B 2017/003* (2013.01); *A61B 2017/00327* (2013.01)

(58) Field of Classification Search
   CPC ... A61M 29/02; A61M 2029/025; A61B 1/04; A61B 1/00082; A61B 1/0052; A61B 1/0055; A61B 1/00135; A61B 17/24
   See application file for complete search history.

(56) References Cited

U.S. PATENT DOCUMENTS

| | | | | |
|---|---|---|---|---|
| 4,615,332 A | * | 10/1986 | Buess ................. | A61B 1/0051 600/113 |
| 4,862,874 A | * | 9/1989 | Kellner .............. | A61B 1/00082 600/116 |
| 5,772,578 A | * | 6/1998 | Heimberger ........ | A61B 1/0056 600/139 |
| 2005/0171400 A1 | * | 8/2005 | Itoi .................... | A61B 1/00082 600/114 |

FOREIGN PATENT DOCUMENTS

JP          2012-528702 A     11/2012
WO     WO-2010/141894 A1    12/2010

* cited by examiner

*Primary Examiner* — Timothy J Neal
(74) *Attorney, Agent, or Firm* — Foley & Lardner LLP (57) ABSTRACT

A treatment instrument for medical use includes a tubular insertion portion that includes a curvable flexible part, the tubular insertion portion being insertable into a body of a patient; and a dilating body that is provided at an outer circumference of the flexible part, the dilating body being configured to dilate in a radial direction relative to the flexible part. The tubular insertion portion includes a reduced-diameter part that is provided at a distal end of the tubular insertion portion in an axial direction, the reduced-diameter part having an outer diameter that is smaller than an outer diameter of the tubular insertion portion at a location proximal of the reduced-diameter part. A distal part of the dilating body is fixed to at least the reduced-diameter part.

10 Claims, 8 Drawing Sheets

TREATMENT INSTRUMENT FOR MEDICAL USE

CROSS-REFERENCE TO RELATED APPLICATION

This application claims priority to Japanese Patent Application No. 2013-217557, filed on Oct. 18, 2013, which is hereby incorporated by reference in its entirety.

BACKGROUND

The present disclosure relates to a treatment instrument for medical use.

A treatment instrument for medical use is known in which an insertion portion to be inserted into a body is so formed as to be curvable and a dilating body is provided at the outer circumference of this insertion portion (refer to e.g. JP-T-2012-528702).

The treatment instrument for medical use described in JP-T-2012-528702 includes an internal guide member having a shape in which the distal part is preliminarily curved, a shaft (insertion portion) that is formed into a tubular shape in which the internal guide member is provided and is so configured as to be advanceable and retractable along the internal guide member and to be curvable, and a balloon (dilating body) provided at the outer circumference of the shaft. The treatment instrument for medical use is so configured that the balloon can be inserted into a body by moving the shaft along the internal guide member.

However, in the case of related-art treatment instruments for medical use like that described in JP-T-2012-528702, the dilating body is attached to the outer circumferential surface of the insertion portion and therefore the attachment strength of the dilating body against a force in the axial direction cannot be sufficiently ensured. Thus, there is a possibility that the dilating body gets separated from the insertion portion when the dilating body is inserted into a body.

SUMMARY OF INVENTION

One objective of certain embodiments of the present invention is to provide a treatment instrument for medical use which prevents separation of a dilating body from an insertion portion when the dilating body is inserted into a body.

According to one embodiment, a treatment instrument for medical use includes a tubular insertion portion that is at least partially formed of a flexible part capable of curving which is configured to be inserted into a body of a patient, and a dilating body that is provided at an outer circumference of the flexible part which is configured to dialate in the radial direction of the flexible part. The insertion portion includes a reduced-diameter part that is provided at a distal part of the insertion portion in an axial direction and that has an outer diameter reduced toward the distal part. A distal part of the dilating body in the axial direction is fixed to at least the reduced-diameter part.

In one aspect, the distal part of the dilating body is fixed to the reduced-diameter part. Therefore, even when the dilating body is pushed in the axial direction in insertion of the dilating body into a body, the distal part of this dilating body can be pressed against the increased-diameter part on the proximal side relative to the reduced-diameter part. Thus, the attachment strength of the dilating body against a force in the axial direction can be enhanced, and therefore, separation of the dilating body from the insertion portion in insertion of the dilating body into a body can be prevented.

In one aspect, the insertion portion includes an insertion tube having a flexible tube that forms the flexible part and an operating tube that is provided in the insertion tube configured to carry out curving operation of the flexible tube. Furthermore, the operating tube includes a tubular part, and a first moving part and a second moving part that are extended from the tubular part toward the proximal side in the axial direction and are so provided as to be capable of relative movement in the axial direction, and the tubular part is so provided as to protrude from the insertion tube. In addition, the reduced-diameter part is formed by the tubular part of the operating tube.

In one aspect, because the reduced-diameter part is formed by the tubular part of the operating tube, providing the operating tube in the insertion tube can form the reduced-diameter part. Thus, the reduced-diameter part can be easily provided. In addition, because the operating tube is provided at such a position as to protrude from the insertion tube, an operating force by the first moving part and the second moving part of the operating tube can be surely transmitted to the distal part of the insertion tube.

In one aspect, the insertion portion includes an insertion tube having a flexible tube that forms the flexible part, and the reduced-diameter part is provided at a distal part of the insertion tube in the axial direction.

In one aspect, because the reduced-diameter part is provided at the distal part of the insertion tube, the outer diameter of the distal part of the insertion portion can be set small and the insertability of the dilating body into a stenosed part in a body can be enhanced.

In one aspect, the reduced-diameter part is reduced in diameter through multiple stages.

In one aspect, because the reduced-diameter part is reduced in diameter through multiple stages, a stenosed part in a body can be gradually dilated when the insertion portion is inserted into this stenosed part, and the insertability of the dilating body into the stenosed part can be enhanced.

In one aspect, an image information transmitting member having an image information acquiring unit that acquires image information is provided in the insertion portion, and the image information acquiring unit is fixed to the distal part of the insertion portion.

In one aspect, because the image information acquiring unit is fixed to the distal part of the insertion portion, the front side of the insertion portion in the insertion direction can be visually recognized, and the passage of the distal part of the insertion portion through a stenosed part in a body can be visually recognized. Furthermore, the insertion portion can be prevented from being inserted into a site other than a procedure-target site.

In one aspect, the flexible part has a joint structure in which a plurality of tubular bodies are connected, and the dilating body includes a covering part that covers the flexible part and a dilating part that forms a space for dilation together with the covering part.

In one aspect, because the covering part that covers the flexible part is provided, the leakage of fluid from the dilating body out to a lumen of the insertion portion can be prevented and the dilating body can be surely dilated.

In one aspect the covering part has rigidity lower than the rigidity of the flexible part and the dilating part in a curving direction.

In one aspect, because the covering part has rigidity lower than the rigidity of the flexible part of the insertion portion and the dilating part of the dilating body in a curving direction, the curving property of the flexible part can be enhanced.

In one aspect, the distal part of the dilating body covers a distal surface of the reduced-diameter part in the axial direction.

In one aspect, because the distal part of the dilating body covers the distal surface of the reduced-diameter part, the region from the distal surface of the insertion portion to the reduced-diameter part can be continuously covered by the same member due to this distal part. This can enhance the insertability of the dilating body into a stenosed part in a body. Furthermore, the dilating body does not locally press the inside of the body, which can prevent damage to biological tissues.

DETAILED DESCRIPTION

Embodiments of the present invention will be described below based on the drawings.

In the following description, the side inserted into the body of a patient in a treatment instrument for medical use, i.e. the axially-distal side of an insertion portion of the treatment instrument for medical use, will be referred to as the "distal side," and the side of hand operation in the treatment instrument for medical use, i.e. the axially-proximal side of the insertion portion, will be referred to as the "proximal side."

Furthermore, in second and subsequent embodiments, the same constituent members as constituent members described in a first embodiment to be shown below and constituent members having similar functions are given the same numerals as those of constituent members of the first embodiment and description of them is omitted or simplified.

First Embodiment

Figure 1:
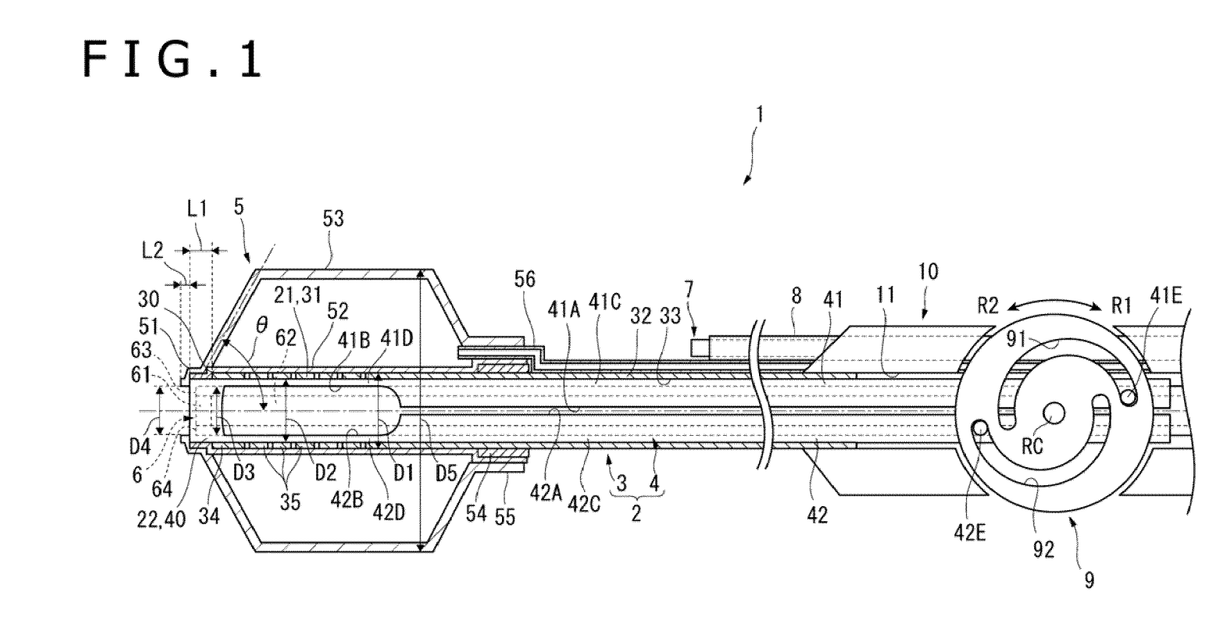
FIG. 1 is a plan view of a treatment instrument for medical use according to a first embodiment of the present invention.

Referring to FIG. 1, a first embodiment of a treatment instrument 1 for medical use includes: a tubular insertion portion 2 that is at least partially formed of a flexible part 21 that is capable of curving and that is configured to be inserted into the body of a patient; a dilating body 5 that is provided at the outer circumference of the flexible part 21 and dilates in the radial direction of this flexible part 21; a first endoscope 6 provided in the insertion portion 2; a guide tube 8 that is provided along the insertion portion 2 and guides a second endoscope 7; an operating member 9 configured to allow and operator to curve the flexible part 21; and a grip portion 10 held by the operator when a medical procedure is performed.

The insertion portion 2 includes an insertion tube 3 having a flexible tube 31 that forms the flexible part 21, a push/pull member 4 that is provided in the insertion tube 3 and serves as an operating tube to carry out curving operation of the flexible tube 31, and a reduced-diameter part 22 that is provided at the distal part of the insertion portion 2 in the axial direction and has an outer diameter reduced toward this distal part.

The insertion tube 3 has the flexible tube 31 provided from a distal part 30 of this insertion tube 3 toward the proximal side, a hard tube 32 having a distal end connected to the flexible tube 31 and a proximal end supported by the grip portion 10, and a lumen 33 that is a continuous space in the flexible tube 31 and the hard tube 32 and is opened to the distal end of the flexible tube 31.

The flexible tube 31 includes plural tubular bodies 34 and 35 and has a joint structure in which these plural tubular bodies 34 and 35 and the hard tube 32 are connected pivotally to each other in the axial direction. An outer diameter D1 of this flexible tube 31 is very small, several millimeters for example, in order to enable introduction into a body. On the other hand, insertion objects such as the push/pull member 4 and the first endoscope 6 are inserted inside the flexible tube 31 and therefore it is preferable that an inner diameter D2 of the flexible tube 31 is set as large as possible. Thus, the outer diameter D1 of the flexible tube 31 is set to about 0.4 to 15 [mm] (preferably 0.7 to 4 [mm]) and the inner diameter D2 is set to about 0.2 to 10 [mm] (preferably 0.4 to 3 [mm]).

The above-described insertion tube 3 is obtained by performing laser processing on a circular tubular member made of stainless steel for example. In the case of using laser processing, by only cutting the circular tubular member by a laser, the insertion tube 3 in the state in which the hard tube 32 and the respective tubular bodies 34 and 35 are connected to each other can be easily obtained. The material and manufacturing method of the insertion tube 3 are not limited to those described above, and other methods and materials can be used.

Figure 2:
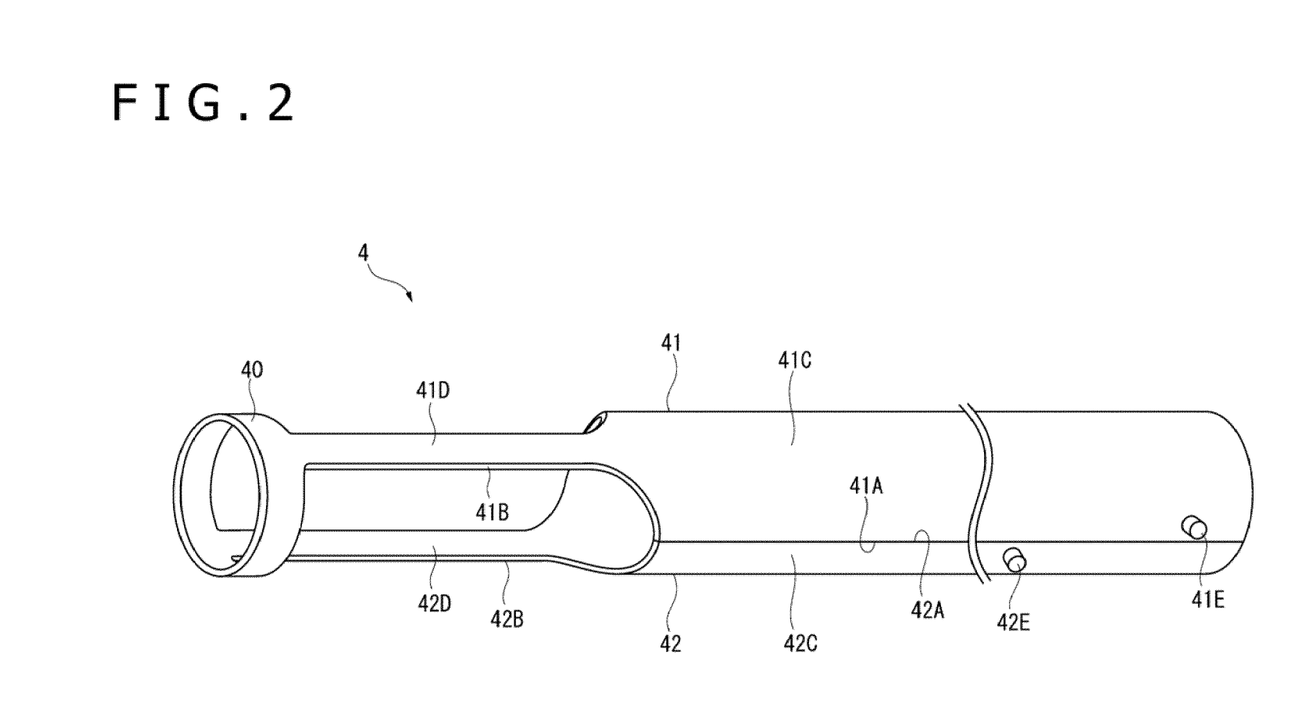
FIG. 2 is a perspective view of an operating tube of the treatment instrument for medical use in FIG. 1.

Also as shown in FIG. 2, the push/pull member 4 includes a tubular part 40 and a first moving part 41 and a second moving part 42 that are extended from the tubular part 40 toward the proximal side and are so provided as to be capable of relative movement in the axial direction of the insertion tube 3. The push/pull member 4 is so configured that the first moving part 41 and the second moving part 42 are pushed and pulled in the axial direction of the insertion tube 3 to thereby cause a curving motion of the flexible tube 31.

The tubular part 40 is fixed to the insertion tube 3 in such a state as to protrude from the insertion tube 3, and the reduced-diameter part 22 is formed by this tubular part 40.

The first moving part 41 and the second moving part 42 are separated from each other in the circumferential direction in the insertion tube 3 and form a tubular structure.

The first moving part 41 has the following parts: notch parts 41B each obtained by notching a circumferentially-end edge 41A of this first moving part 41; a large-width part 41C that is a part at which the notch part 41B is not made and has a shape obtained by dividing a cylindrical member in the circumferential direction; a small-width part 41D that is a part at which the notch parts 41B are provided and is formed with a smaller width than the large-width part 41C by the notch parts 41B; and a first protrusion 41E that is provided at the large-width part 41C and protrudes in a direction perpendicular to the end edges 41A.

The notch parts 41B are formed by notching the end edges 41A on both sides in the circumferential direction into the same shape at the same position in the axial direction. In the present embodiment, the notch parts 41B are formed between the tubular part 40 and the large-width part 41C.

The large-width part 41C is formed into a shape obtained by bisecting a cylindrical member evenly in the circumferential direction. The circumferentially-end edges 41A of this large-width part 41C are formed into a straight line shape and are in slide contact with end edges 42A of the adjacent second moving part 42 along the axial direction. That is, the first moving part 41 and the second moving part 42 are so formed that the circumferentially-end edges 41A and 42A except for the notch parts 41B and 42B, respectively, are in slide contact with each other along the axial direction.

The small-width part 41D is extended along the axial direction at substantially the center position of the first moving part 41 in the circumferential direction and is so formed that its dimensions in the circumferential direction are constant in the axial direction.

The second moving part 42 has the same configuration as the first moving part 41 except for that a second protrusion 42E is provided instead of the first protrusion 41E and can be explained by substituting numerals 42 for numerals 41 in the above description about the first moving part 41. Therefore, description of the respective parts other than the second protrusion 42E is omitted.

The second protrusion 42E protrudes in a direction that is perpendicular to the end edges 42A and is the same as the protrusion direction of the first protrusion 41E of the first moving part 41. This second protrusion 42E is provided on the distal side relative to a rotation center RC of the operating member 9 (distal side relative to the first protrusion 41E) in a state in which the flexible tube 31 is not curved.

In the above push/pull member 4, by making the first moving part 41 and the second moving part 42 relatively move in the axial direction, the two small-width parts 41D and 42D opposed to each other curve in the plane passing through these two small-width parts 41D and 42D to thereby curve the flexible tube 31. Because the push/pull member 4 is provided in the flexible tube 31, its outer diameter needs to be set to be very small, several millimeters for example. On the other hand, insertion objects such as the first endoscope 6 are inserted inside the push/pull member 4 and therefore it is preferable that an inner diameter D3 of the push/pull member 4 be as large as possible. Thus, the outer diameter of the push/pull member 4 is set equivalent to the inner diameter D2 of the flexible tube 31, and the inner diameter D3 is set to about 0.1 to 5 [mm] (preferably 0.2 to 2.5 [mm]).

The dilating body 5 includes: a distal part 51 that is provided on the distal side of this dilating body 5 and is fixed to the reduced-diameter part 22 of the insertion portion 2; a covering part 52 that covers the flexible tube 31; a dilating part 53 that forms a space for dilation together with the covering part 52; and a movable part 54 that is provided at a proximal part 55 of the dilating body 5 in the axial direction and can move this proximal part 55 along the insertion tube 3.

The distal part 51 covers the distal surface of the reduced-diameter part 22, and the outer diameter of the part thereof on the distal side relative to the reduced-diameter part 22 is smaller than the reduced-diameter part 22. In the distal part 51, a length L1 of the part fixed to the circumferential surface of the reduced-diameter part 22 in the axial direction (length of the reduced-diameter part 22 in the axial direction) is set to about 0.05 to 10 [mm] (preferably 1 to 3 [mm]). Furthermore, in the distal part 51, in order to ensure the field of view of the first endoscope 6, a length L2 of the part covering the distal surface of the reduced-diameter part 22 in the axial direction is set to about 0.01 to 2 [mm] (preferably 0.05 to 0.5 [mm]), and an inner diameter D4 of this part is set to about 0.1 to 5 [mm] (preferably 0.2 to 2 [mm]).

The covering part 52 is formed of a material having higher flexibility than the dilating part 53. Examples of the material include: elastic members such as rubber and resins, polyolefins such as polyethylene, polypropylene, polybutene, ethylene-propylene copolymer, ethylene-vinyl acetate copolymer, and ionomer, cross-linked or partially-cross-linked substances of them, polyester such as polyethylene terephthalate, polyester elastomer, polyvinyl chloride, polyurethane, polyurethane elastomer, polyphenylene sulfide, polyamide, polyamide elastomer, polymer materials such as fluorine resins, silicone rubber, and latex rubber. The covering part 52 has rigidity lower than the rigidity of the flexible tube 31 and the dilating part 53 in a curving direction.

The dilating part 53 is formed of a flexible material similar to that of the covering part 52. An outer diameter D5 of the dilating part 53 when it is dilated is set to about 2 to 30 [mm] (preferably 3.5 to 10 [mm]) and an inclination angle θ of the distal side is set to about 20 to 90 [deg] (preferably 45 to 80 [deg]).

The movable part 54 is formed of a material that can easily slide, such as a metal or resin, and is provided slidably on the outer circumferential surface of the hard tube 32. The movable part 54 may be formed monolithically with the dilating part 53 and form part of the proximal part 55.

The above dilating body 5 communicates with a fluid delivery path 56 made along the insertion tube 3 and is so configured as to dilate in the radial direction through introduction of fluid into the dilating body 5 via this fluid delivery path 56. The fluid delivery path 56 is connected to the proximal part 55 of the dilating body 5 and is formed movably in the axial direction of the insertion tube 3 together with this proximal part 55.

The first endoscope 6 has an image information acquiring unit 61 formed of an optical system such as an objective lens and an imaging element such as a charge coupled device (CCD) image sensor. The first endoscope 6 includes an image information transmitting member 62, an optical transmitter 63, such as an optical fiber, to transmit light toward the distal part of this first endoscope 6, and a lumen 64 whose distal end is opened for suction cleaning. This first endoscope 6 may be so configured as to be curvable by an operating measure such as a wire (not shown) connected to the distal part of this first endoscope 6. Furthermore, the image information acquiring unit 61 may be a digital video camera using another imaging element such as a complementary metal oxide semiconductor (CMOS) image sensor. Moreover, the image information transmitting member 62 is formed of an electrical wire that transmits an electrical signal, such as a metal line, if an imaging element such as an image sensor is used for the image information acquiring unit 61. However, the image information transmitting member 62 is not limited thereto and may be an image fiber to carry out image acquisition and image transmission by using an optical fiber or an imaging system to carry out image transmission by an objective lens and plural relay lens optical systems.

The second endoscope 7 has a configuration similar to that of the first endoscope 6 and therefore description thereof is omitted. The second endoscope 7 may have a configuration obtained by removing the lumen 64 for suction cleaning from the configuration of the first endoscope 6.

The operating member 9 is formed of a circular disc member. A first guide groove 91 with which the first protrusion 41E provided at the first moving part 41 engages and a second guide groove 92 with which the second protrusion 42E provided at the second moving part 42 engages are formed in the disc surface. In addition, recesses and projections (not shown) are made on the outer circumferential surface of the disc member. This operating member 9 is so provided as to be capable of rotating with the rotation center being an axis along a direction perpendicular to the axial direction of the insertion tube 3, and is so configured that the movement of the first moving part 41 and the second moving part 42 can be operated by rotating the operating member 9.

The first guide groove 91 and the second guide groove 92 are each formed into an arc shape of a true circle and are made at such positions as to sandwich the rotation center RC of the operating member 9 with the inside of the arc of each groove oriented toward the rotation center RC.

The center of curvature of the first guide groove 91 is set at a position separate from the rotation center RC toward the end side of this first guide groove 91 in a direction R1. Furthermore, the first guide groove 91 is formed into such a shape that its end part in a direction R2 is set at a position closer to the rotation center RC than its end part in the direction R1 and the distance from the rotation center RC progressively increases in the direction R1. That is, the first guide groove 91 is so formed as to move the first moving part 41 toward the distal side when the operating member 9 rotates in the direction R1 and move the first moving part 41 toward the proximal side when the operating member 9 rotates in the direction R2.

The center of curvature of the second guide groove 92 is set at a position separate from the rotation center RC toward the end side of this second guide groove 92 in the direction R1 (opposite side to the center of curvature of the first guide groove 91). Furthermore, the second guide groove 92 is formed into such a shape that its end part in the direction R2 is set at a position closer to the rotation center RC than its end part in the direction R1 and the distance from the rotation center RC progressively increases in the direction R1. That is, the second guide groove 92 is so formed as to move the second moving part 42 toward the proximal side when the operating member 9 rotates in the direction R1 and move the second moving part 42 toward the distal side when the operating member 9 rotates in the direction R2.

The grip portion 10 is formed of a material such as a hard resin and supports the insertion portion 2, the guide tube 8, and the operating member 9. A through-hole 11 into which the first endoscope 6 is inserted is made in this grip portion 10 and the insertion tube 3 is supported by the grip portion 10 in a state in which the proximal part of the insertion tube 3 is inserted into the through-hole 11.

Next, as one example, a method of using the treatment instrument 1 for medical use when the treatment instrument 1 for medical use is used as a treatment instrument for therapy of sinusitis will be described.

First, an operator inserts the insertion portion 2 of the treatment instrument 1 for medical use into a nostril. At this time, the operator can insert the insertion portion 2 while checking the condition in the insertion path based on image information acquired by the image information acquiring unit 61. Furthermore, the operator can curve the flexible tube 31 in accordance with the shape of the insertion path.

Figure 3:
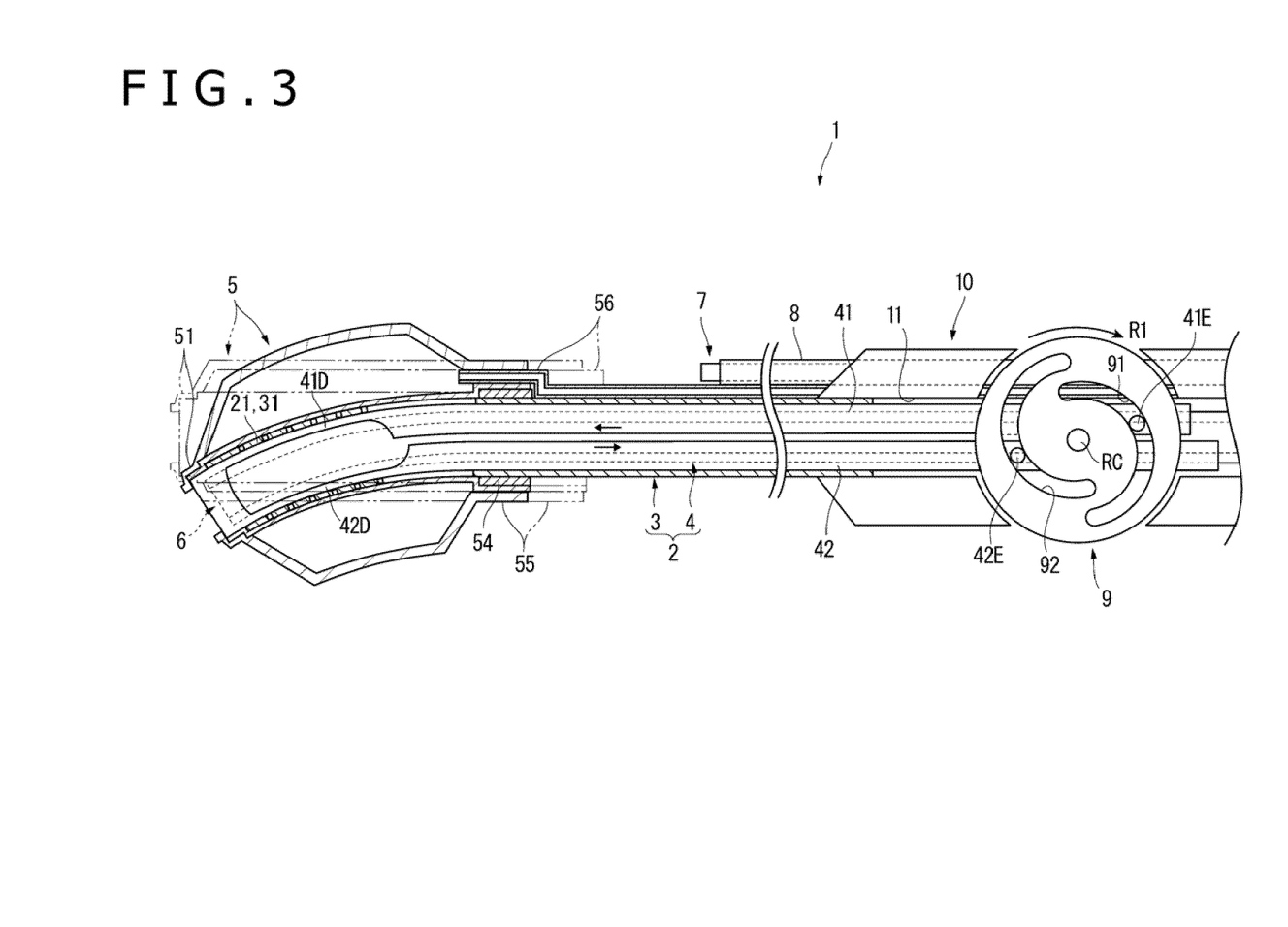
FIG. 3 is an explanatory diagram of the operation of the treatment instrument for medical use in FIG. 1

In the case of curving the flexible tube 31, the operating member 9 is rotated. For example, as shown in FIG. 3, when the operating member 9 is rotated in the direction R1, the first moving part 41 moves toward the distal side due to guiding of the first protrusion 41E by the first guide groove 91, and the second moving part 42 moves toward the proximal side due to guiding of the second protrusion 42E by the second guide groove 92. Due to this, the first moving part 41 is pushed toward the distal side and the second moving part 42 is pulled toward the proximal side, so that the small-width parts 41D and 42D curve downward, causing the flexible tube 31 to curve downward.

After the insertion portion 2 is introduced into a natural ostium of a paranasal sinus stenosed due to sinusitis, the operator inserts the dilating body 5 into the stenosed part of the natural ostium.

The distal part 51 of the dilating body 5 is fixed to the reduced-diameter part 22. This can enhance the attachment strength of the dilating body 5 and prevent separation of the dilating body 5 from the insertion tube 3. Furthermore, the distal part 51 of the dilating body 5 covers the distal surface of the reduced-diameter part 22, which can enhance the insertability of the dilating body 5 into the stenosed part of the natural ostium.

After the dilating body 5 is inserted into the stenosed part of the natural ostium, the operator introduces fluid into the dilating body 5 and dilates the dilating body 5 to thereby perform a dilation therapy for the stenosed part of the natural ostium.

In the dilating body 5, only the distal part 51 is fixed to the insertion tube 3 whereas the proximal part 55 of the dilating body 5 is provided movably in the axial direction relative to the insertion tube 3 with the intermediary of the movable part 54. Therefore, when the dilating body 5 is dilated in a state in which the flexible tube 31 is curved, the proximal part 55 of the dilating body 5 is pulled toward the distal side of the insertion tube 3, so that the proximal part 55 moves toward the distal side of the insertion tube 3 as shown in FIG. 3. This can prevent the deformation of the dilating body 5. Thus, the dilating body 5 can be properly dilated even when the dilating body 5 is dilated in a state in which the flexible tube 31 is curved.

According to the present embodiment described above, the following effects are achieved.

Specifically, because the distal part 51 of the dilating body 5 is fixed to the reduced-diameter part 22, even when the dilating body 5 is pushed in the axial direction, the distal part 51 of this dilating body 5 can be pressed against the increased-diameter part on the proximal side relative to the reduced-diameter part 22. Thus, the attachment strength of the dilating body 5 against a force in the axial direction can be enhanced and therefore separation of the dilating body 5 from the insertion portion 2 in insertion of the dilating body 5 into a body can be prevented.

Furthermore, because the reduced-diameter part 22 is formed by the tubular part 40 of the push/pull member 4, providing the push/pull member 4 in the insertion tube 3 can form the reduced-diameter part 22. Thus, the reduced-diameter part 22 can be easily provided. In addition, because the push/pull member 4 is provided at such a position as to protrude from the insertion tube 3, an operating force by the first moving part 41 and the second moving part 42 of the push/pull member 4 can be surely transmitted to the distal part 30 of the insertion tube 3.

Moreover, because the image information acquiring unit 61 is fixed to the distal part of the insertion portion 2, the front side of the insertion portion 2 in the insertion direction can be visually recognized and the passage of the distal part of the insertion portion 2 through a stenosed part in a body can be visually recognized. Furthermore, the insertion portion 2 can be prevented from being inserted into a site other than a procedure-target site.

In addition, because the covering part 52 that covers the flexible tube 31 is provided, the leakage of the fluid in the dilating body 5 out to the lumen 33 of the insertion tube 3 can be prevented and the dilating body 5 can be surely dilated.

Furthermore, because the covering part 52 has rigidity lower than the rigidity of the flexible tube 31 and the dilating part 53 in a curving direction, the curving property of the flexible part 21 can be enhanced.

Moreover, because the distal part 51 of the dilating body 5 covers the distal surface of the reduced-diameter part 22, the region from the distal surface of the insertion portion 2 to the reduced-diameter part 22 can be continuously covered by the same member due to this distal part. This can enhance the insertability of the dilating body 5 into a stenosed part in a body. Furthermore, the dilating body 5 does not locally press the inside of the body, which can prevent damage to biological tissues.

Second Embodiment

Figure 4:
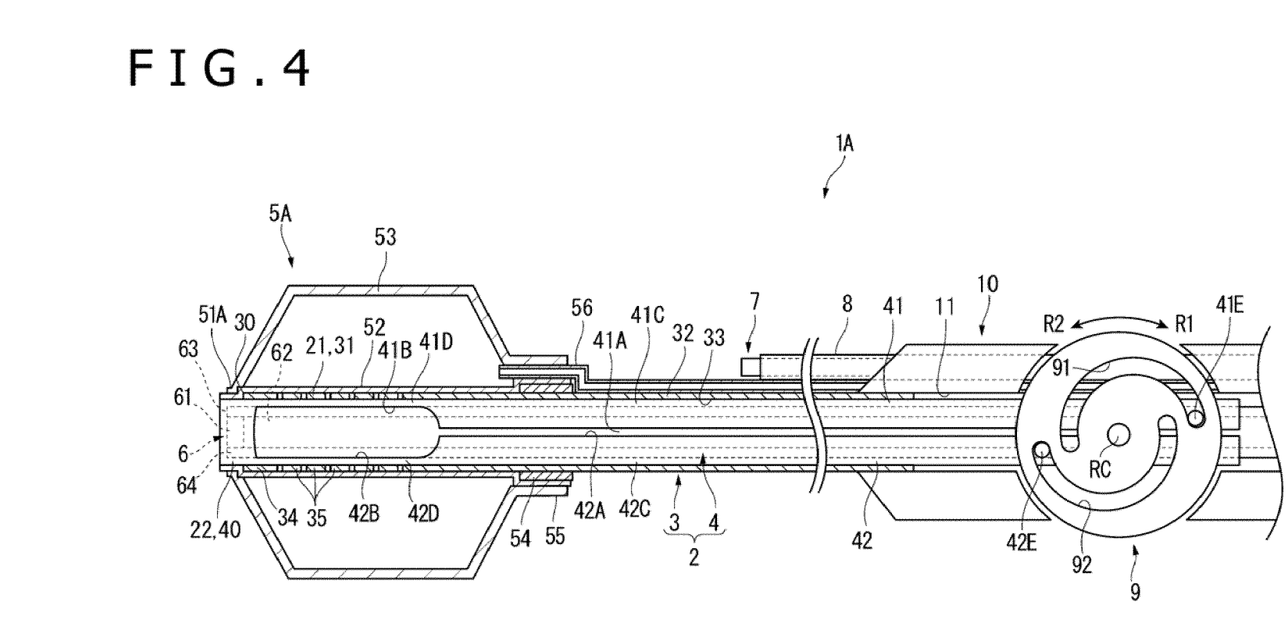
FIG. 4 is a plan view of a treatment instrument for medical use according to a second embodiment of the present invention.

As shown in FIG. 4, a treatment instrument 1A for medical use according to a second embodiment of the present invention is different from that of the first embodiment in that a distal part 51A of a dilating body 5A does not cover the distal surface of the reduced-diameter part 22.

According to the present embodiment, the following effect can be achieved in addition to the effects of the first embodiment.

Specifically, because the configuration in which the distal part 51A of the dilating body 5A does not cover the distal surface of the reduced-diameter part 22 is employed, the shape of the dilating body 5A can be simplified and the treatment instrument 1A for medical use can be manufactured more easily.

Third Embodiment

Figure 5:
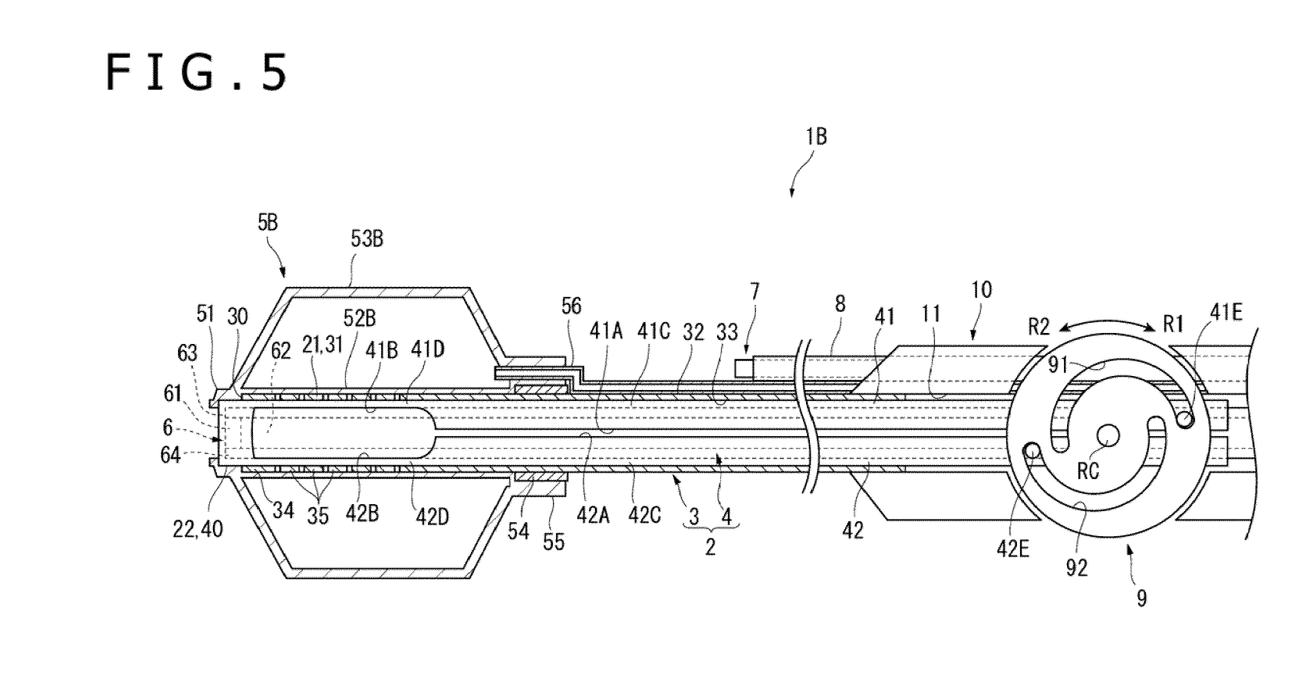
FIG. 5 is a plan view of a treatment instrument for medical use according to a third embodiment of the present invention.

As shown in FIG. 5, a treatment instrument 1B for medical use according to a third embodiment of the present invention is different from that of the first embodiment in that a covering part 52B and a dilating part 53B of a dilating body 5B are monolithically formed by the same material.

The covering part 52B and the dilating part 53B are formed of any of materials similar to those in the first embodiment.

According to the present embodiment, the following effect can be achieved in addition to the effects of the first embodiment.

Specifically, because the covering part 52B and the dilating part 53B of the dilating body 5B are formed of the same material, the number of materials to form the dilating body 5B can be reduced.

Fourth Embodiment

Figure 6:
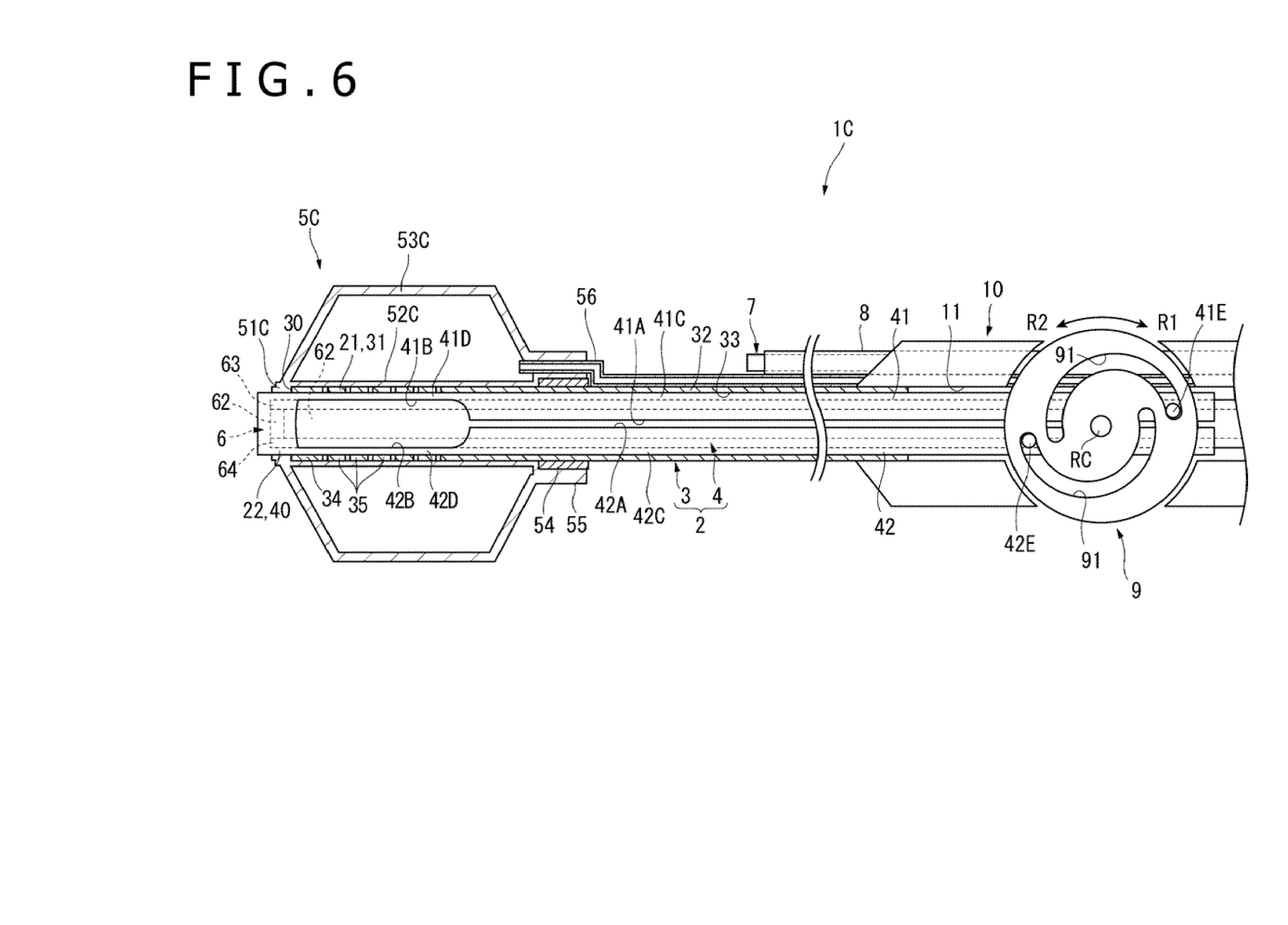
FIG. 6 is a plan view of a treatment instrument for medical use according to a fourth embodiment of the present invention.

As shown in FIG. 6, a treatment instrument 1C for medical use according to a fourth embodiment of the present invention is different from that of the first embodiment in that a covering part 52C and a dilating part 53C of a dilating body 5C are monolithically formed by the same material and that a distal part 51C of the dilating body 5C does not cover the distal surface of the reduced-diameter part 22.

The covering part 52C and the dilating part 53C are formed of a material similar to that of the covering part 52B and the dilating part 53B in the second embodiment.

According to the present embodiment, the effects of the second embodiment and the third embodiment are achieved in addition to the effects of the first embodiment.

Fifth Embodiment

Figure 7:
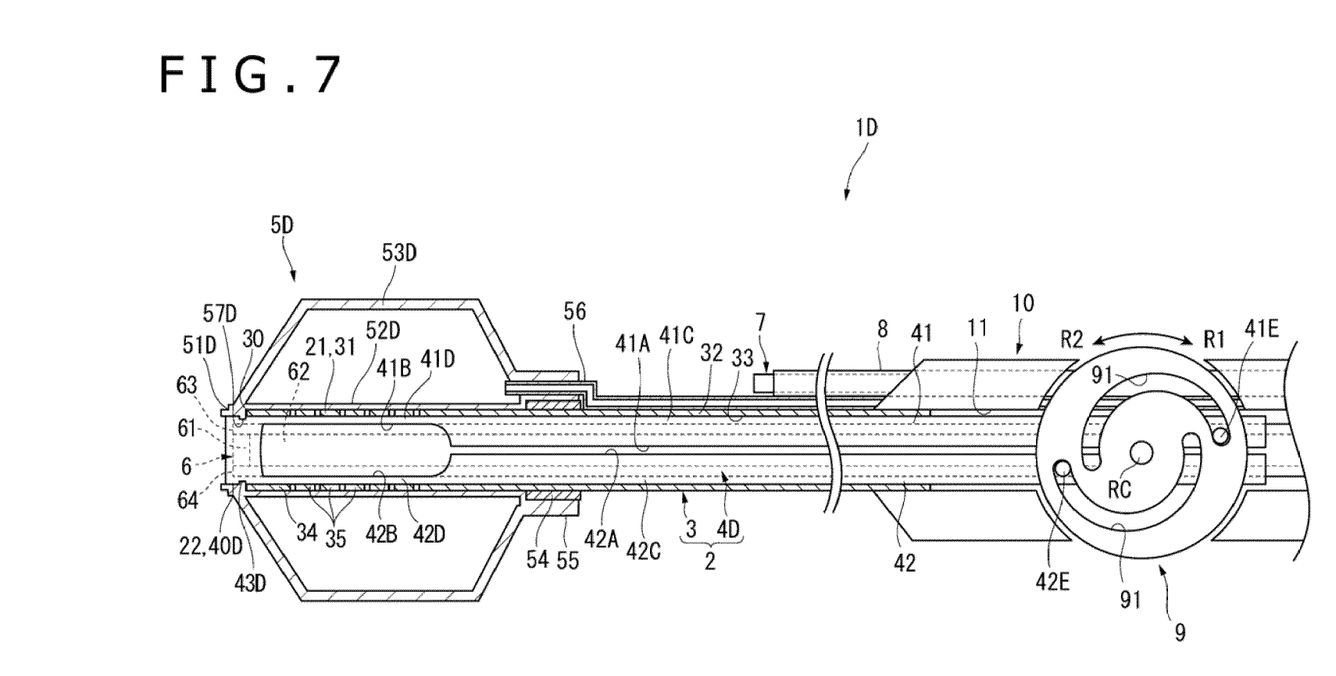
FIG. 7 is a plan view of a treatment instrument for medical use according to a fifth embodiment of the present invention.

As shown in FIG. 7, a treatment instrument 1D for medical use according to a fifth embodiment of the present invention is different from that of the first embodiment in the following three points. First, a groove 43D along the circumferential direction is formed in the outer circumferential surface of a tubular part 40D of a push/pull member 4D. Second, a covering part 52D and a dilating part 53D of a dilating body 5D are monolithically formed by the same material. Third, a locking part 57D is so provided as to protrude from the inner circumferential surface of a distal part 51D of the dilating body 5D to be locked to the groove 43D of the push/pull member 4D.

The locking part 57D may be formed continuously in the circumferential direction in the inner circumferential surface of the distal part 51D of the dilating body 5D or may be provided intermittently in the circumferential direction.

The covering part 52D and the dilating part 53D are formed of a material similar to that of the covering part 52B and the dilating part 53B in the second embodiment.

According to the present embodiment, the following effect is achieved in addition to the effects of the first embodiment to the third embodiment.

Specifically, because the locking part 57D of the dilating body 5D is locked to the groove 43D of the push/pull member 4D, the attachment strength of the dilating body 5D against a force in the axial direction can be further enhanced.

Sixth Embodiment

Figure 8:
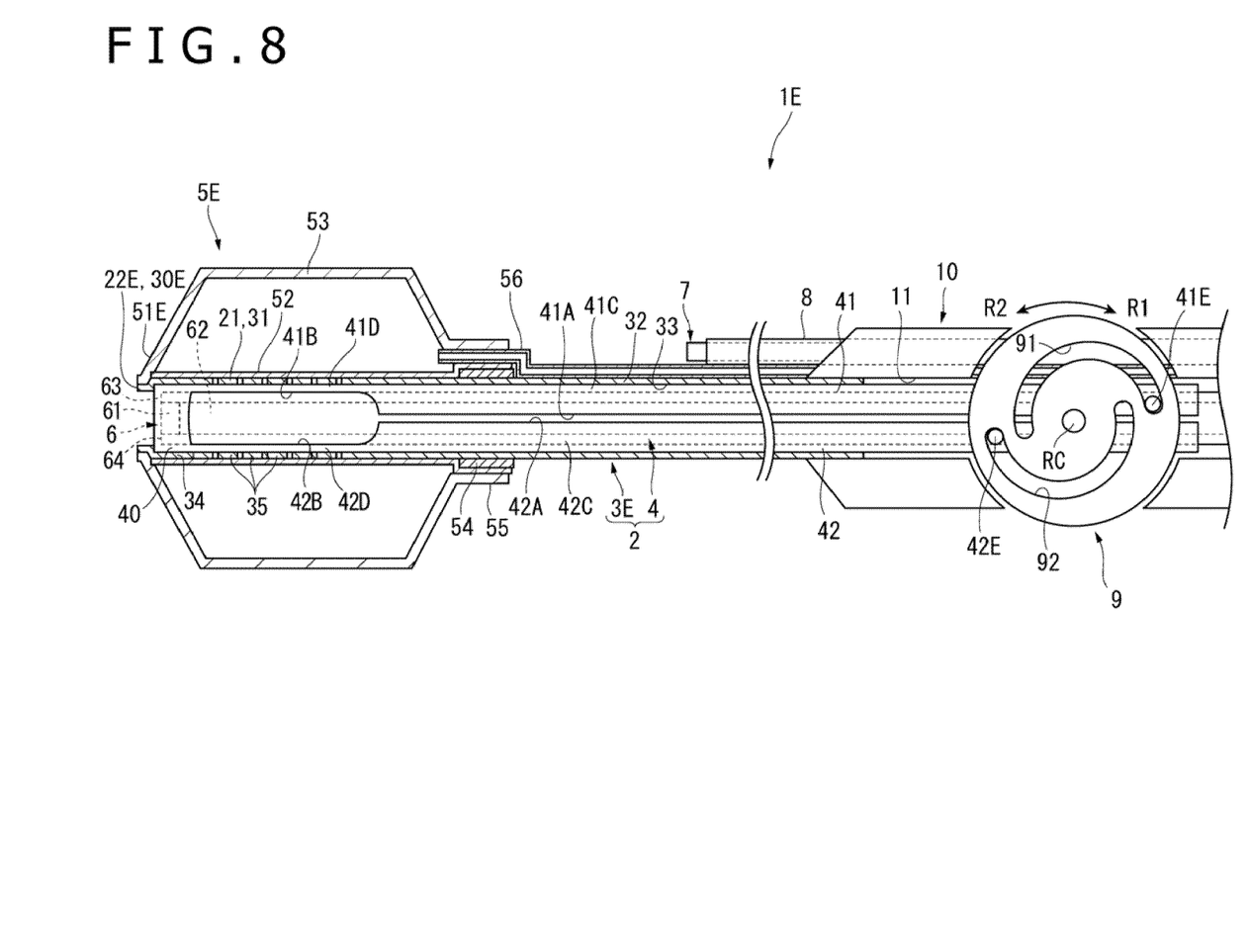
FIG. 8 is a plan view of a treatment instrument for medical use according to a sixth embodiment of the present invention.

As shown in FIG. 8, a treatment instrument 1E for medical use according to a sixth embodiment of the present invention is different from that of the first embodiment in that a reduced-diameter part 22E is made at a distal part 30E of an insertion tube 3E and a distal part 51E of a dilating body 5E does not cover the distal surface of the reduced-diameter part 22E.

The distal part 30E of the insertion tube 3E covers the distal surface of the tubular part 40 of the push/pull member 4 and its outer diameter is smaller than that of the insertion tube 3E on the proximal side relative to the distal part 30E.

According to the present embodiment, the same effects as those of the first embodiment are achieved.

The present invention is not limited to the above-described embodiments and modifications, improvements, and so forth within such a range that the object of the present invention can be achieved are included in the present invention.

For example, the reduced-diameter part 22 may be reduced in diameter through multiple stages. This allows a stenosed part in a body to gradually dilate when the insertion portion 2 is inserted into this stenosed part and enables enhancement in the insertability of the dilating body 5 into the stenosed part.

Any object can be used as the insertion tube 3 or 3E as long as it is so made that at least part thereof is curvable. For example, the whole of the insertion tube 3 or 3E may be formed of the flexible tube 31. Furthermore, the flexible tube 31 may be formed by a material having flexibility or the whole of the insertion tube 3 may be formed by this material having flexibility. In this case, the insertion tube 3 does not need to have a cylindrical shape and may be an object whose section has a polygonal shape.

The push/pull member 4 or 4D is not limited to that of the above-described embodiment. For example, the tubular part 40 or 40D may be formed into a ring shape. Furthermore, the tubular part 40 or 40D may be bisected in the circumferential direction and the resulting sections may be formed as part of the first moving part 41 and the second moving part 42.

Any shape can be employed as the shape of the operating member 9 as long as the operating member 9 allows relative movement of the first moving part 41 and the second moving part 42 along the axial direction of the insertion tube 3 or 3E. For example, a first protrusion and a second protrusion may be provided on the operating member 9, and a first guide groove may be made in the first moving part 41 and a second guide groove may be made in the second moving part 42. Alternatively, the first guide groove may be made in the first moving part 41 and the second protrusion may be provided on the second moving part 42, and the first protrusion and the second guide groove may be made in the operating member 9. Alternatively, the opposite combination may be employed.

The first guide groove 91 and the second guide groove 92 may be formed into a recessed shape without penetrating the operating member 9.

When the operating member 9 is rotated in the direction R1, the flexible tube 31 may curve upward.

Although the fluid delivery path 56 is provided along the insertion tube 3 or 3E, the configuration is not limited thereto. For example, it may be wound around the insertion tube 3 or 3E or may be so formed as to be expandable and contractable in the axial direction of the insertion tube 3 or 3E.

It should be understood by those skilled in the art that various modifications, combinations, sub-combinations and alterations may occur depending on design requirements and other factors insofar as they are within the scope of the appended claims or the equivalents thereof.

What is claimed is:

1. A treatment instrument for medical use, comprising:
    a tubular insertion portion that is insertable into a body of a patient, the tubular insertion portion comprising:
        an insertion tube that comprises a curvable flexible tube; and
        an operating tube located in the insertion tube and configured to operably cause the flexible tube to curve, the operating tube comprising:
            a tubular part that is fixed to the insertion tube, protrudes from a distal end of the insertion tube, and has a diameter that is smaller than a diameter of the insertion tube, and
            a first moving part and a second moving part that extend proximally from the tubular part, the first and second moving parts being movable relative to one another in an axial direction;
    a dilating body that is provided at an outer circumference of the flexible tube, the dilating body being configured to dilate in a radial direction relative to the flexible tube;
    wherein a distal part of the dilating body is fixed to at least the tubular part of the operating tube.

2. The treatment instrument for medical use according to claim 1, wherein the tubular insertion portion further comprises an image information transmitting member comprising an image information acquiring unit configured to acquire image information.

3. The treatment instrument for medical use according to claim 2, wherein the image information acquiring unit is fixed to the distal part of the tubular insertion portion.

4. The treatment instrument for medical use according to claim 1, wherein the flexible tube comprises a plurality of tubular bodies connected in a joint structure.

5. The treatment instrument for medical use according to claim 1, wherein the dilating body comprises:
    a covering part that at least partially covers the flexible part, and
    a dilating part, which together with the covering part, forms a space for dilation.

6. The treatment instrument for medical use according to claim 5, wherein the covering part has a rigidity lower than a rigidity of the flexible part and the dilating part in a direction in which the operating tube is configured to operably cause the flexible tube to curve.

7. The treatment instrument for medical use according to claim 1, wherein the distal part of the dilating body covers a distal surface of the tubular part of the operating tube.

8. The treatment instrument for medical use according to claim 1, wherein the dilating body comprises a movable part provided at a proximal part of the dilating body, the movable part being configured to slidably move along the tubular insertion portion.

9. The treatment instrument for medical use according to claim 1, wherein the insertion tube further comprises a hard tube.

10. The treatment instrument for medical use according to claim 1, further comprising a fluid delivery path configured to introduce fluid into the dilating body in order to dilate the dilating body.

* * * * *